US012622968B2

(12) United States Patent
Plassat et al.

(10) Patent No.: US 12,622,968 B2
(45) Date of Patent: May 12, 2026

(54) FORMULATION FOR ORAL DELIVERY OF PROTEINS, PEPTIDES AND SMALL MOLECULES WITH POOR PERMEABILITY

(71) Applicants: R.P. Scherer Technologies, LLC, Carson City, NV (US); Pfizer Ireland Pharmaceuticals, Ringaskiddy (IE)

(72) Inventors: Vincent Plassat, La Ferté Alais (FR); Benoit Hilbold, Schiltigheim (FR); Aurélia Galus, Weyersheim (FR); Thomas Pointeaux, Reichstett (FR); Julien Meissonnier, Souffelweyersheim (FR); Gene M. Dubowchik, New Haven, CT (US); Charles M. Conway, New Haven, CT (US); Rajesh Kumar, New Haven, CT (US)

(73) Assignees: R.P. Scherer Technologies, LLC, Carson City, NV (US); Pfizer Ireland Pharmaceuticals, Ringaskiddy (IE)

( * ) Notice: Subject to any disclaimer, the term of this patent is extended or adjusted under 35 U.S.C. 154(b) by 1055 days.

(21) Appl. No.: 17/602,915

(22) PCT Filed: Apr. 10, 2020

(86) PCT No.: PCT/US2020/027800
§ 371 (c)(1),
(2) Date: Oct. 11, 2021

(87) PCT Pub. No.: WO2020/210722
PCT Pub. Date: Oct. 15, 2020

(65) Prior Publication Data

US 2022/0249468 A1 Aug. 11, 2022

Related U.S. Application Data

(60) Provisional application No. 62/832,508, filed on Apr. 11, 2019.

(51) Int. Cl.

| | |
|---|---|
| ***A61K 47/14*** | (2017.01) |
| ***A61K 31/496*** | (2006.01) |
| ***A61K 38/03*** | (2006.01) |
| ***A61K 47/26*** | (2006.01) |
| ***A61K 47/34*** | (2017.01) |
| ***C07K 16/18*** | (2006.01) |

(52) U.S. Cl.
CPC ............ *A61K 47/14* (2013.01); *A61K 31/496* (2013.01); *A61K 38/03* (2013.01); *A61K 47/26* (2013.01); *A61K 47/34* (2013.01); *C07K 16/18* (2013.01)

(58) Field of Classification Search
CPC ...... A61K 47/14; A61K 31/496; A61K 38/03; A61K 47/26; A61K 47/34; A61K 38/00; A61K 9/10; A61K 39/39591; A61K 9/08; C07K 16/18
See application file for complete search history.

(56) References Cited

U.S. PATENT DOCUMENTS

| | | | |
|---|---|---|---|
| 6,096,338 A | 8/2000 | Lacy et al. | |
| 8,323,695 B2 | 12/2012 | Huang et al. | |
| 8,481,546 B2 | 7/2013 | Chaturvedula | |
| 8,859,623 B1 | 10/2014 | Witham et al. | |
| 9,259,389 B2 | 2/2016 | Meissonnier et al. | |
| 9,308,166 B2 | 4/2016 | Agisim et al. | |
| 11,185,589 B2 * | 11/2021 | Plassat | A61K 47/26 |
| 2002/0032171 A1 | 3/2002 | Chen et al. | |
| 2003/0082215 A1 | 5/2003 | Lemut | |
| 2005/0079145 A1 * | 4/2005 | Constantinides | A61P 5/06 424/70.31 |
| 2005/0249802 A1 | 11/2005 | Khanolkar et al. | |
| 2007/0298099 A1 | 12/2007 | Peresypkin et al. | |
| 2008/0014274 A1 | 1/2008 | Bubnis et al. | |
| 2008/0260840 A1 | 10/2008 | Alessi et al. | |
| 2010/0210568 A1 | 8/2010 | Bevec | |
| 2012/0059017 A1 | 3/2012 | Chaturvedula | |
| 2012/0316132 A1 | 12/2012 | Meissonnier et al. | |
| 2013/0309226 A1 | 11/2013 | Armstrong et al. | |
| 2015/0147399 A1 | 5/2015 | Vol et al. | |

(Continued)

FOREIGN PATENT DOCUMENTS

| | | |
|---|---|---|
| CA | 2439366 A1 | 9/2002 |
| CN | 1635911 A | 7/2005 |

(Continued)

OTHER PUBLICATIONS

Office Action dated Aug. 14, 2023, directed to TW Application No. 109112175; 10 pages.
Office Action dated Aug. 3, 2023, directed to SG Application No. 11202111251S; 7 pages.
Office Action dated Jul. 17, 2023, directed to EA Application No. 202192793/28; 8 pages.
Office Action dated Jun. 23, 2023, directed to IN Application No. 202127050600; 7 pages.
Office Action dated Jun. 7, 2023, directed to EA Application No. 202192792/28; 4 pages.
Office Action dated Sep. 12, 2023, directed to IN Application No. 202127050601; 6 pages.
Office Action dated Sep. 27, 2023, directed to SA Application No. 521430528; 10 pages.

(Continued)

*Primary Examiner* — Joseph K Mckane
*Assistant Examiner* — Meghan C Heasley
(74) *Attorney, Agent, or Firm* — Morrison & Foerster LLP

(57) ABSTRACT

The present disclosure is directed to a pharmaceutical formulation intended for oral delivery of synthetic or natural poorly permeable calcitonin gene-related peptide (CGRP) inhibitors or salts/solvates thereof having a therapeutic activity. The pharmaceutical formulation can include a synthetic or natural poorly permeable CGRP inhibitors or salt or solvate thereof in an amount 0.01-10 wt. % of the total weight of the formulation; a lipophilic phase comprising triglycerides of fatty acids in an amount of 50-80 wt. % of the total weight of the formulation; and at least one lipophilic surfactant comprising partial esters of polyol and fatty acids in an amount of about 10-50 wt. % of the total weight of the formulation.

14 Claims, 2 Drawing Sheets

(56) References Cited

U.S. PATENT DOCUMENTS

| | | | | |
|---|---|---|---|---|
| 2015/0165032 | A1 | 6/2015 | Ailhas et al. | |
| 2017/0037117 | A1* | 2/2017 | Dillin | A61P 3/10 |
| 2017/0100355 | A1 | 4/2017 | Cavatur et al. | |
| 2018/0092899 | A1 | 4/2018 | Liu | |
| 2020/0323985 | A1 | 10/2020 | Plassat | |

FOREIGN PATENT DOCUMENTS

| | | | | |
|---|---|---|---|---|
| CN | 101048137 | A | 10/2007 | |
| CN | 101511184 | A | 8/2009 | |
| GB | 2228198 | A | 8/1990 | |
| JP | H6-509796 | A | 11/1994 | |
| JP | 2005-515197 | A | 5/2005 | |
| JP | 2008-521807 | A | 6/2008 | |
| JP | 2013-514336 | A | 4/2013 | |
| KR | 10-2007-0084531 | A | 8/2007 | |
| WO | 93/02664 | A1 | 2/1993 | |
| WO | 94/19003 | A1 | 9/1994 | |
| WO | 99/43299 | A2 | 9/1999 | |
| WO | 03/047493 | A2 | 6/2003 | |
| WO | 2006/057903 | A2 | 6/2006 | |
| WO | WO-2011123232 | A1 * | 10/2011 | A61K 31/416 |
| WO | 2013/124415 | A1 | 8/2013 | |
| WO | 2015/127416 | A1 | 8/2015 | |
| WO | 2016/071756 | A1 | 5/2016 | |
| WO | 2017/093810 | A2 | 6/2017 | |

OTHER PUBLICATIONS

Office Action dated Sep. 27, 2023, directed to SA Application No. 521430537; 9 pages.
Plassat et al., U.S. Office Action dated May 25, 2023, directed to U.S. Appl. No. 17/536,452; 17 pages.
Search Report and Written Opinion dated Aug. 21, 2023, directed to SG Application No. 11202110546U; 12 pages.
Office Action dated Oct. 10, 2024, directed to AE Application No. 2021-6001840; 8 pages.
Office Action dated Sep. 12, 2024, directed to SA Application No. 521430528; 9 pages.
Office Action dated Sep. 17, 2024, directed to JP Application No. 2021-559862; 6 pages.
Office Action dated Sep. 3, 2024, directed to PH Application No. 1-2021-552591; 4 pages.
Plassat et al. U.S. Office Action dated Sep. 6, 2024, directed to U.S. Appl. No. 17/536,452; 15 pages.
Search Report dated Sep. 12, 2024, directed to AE Application No. P60018372021; 2 pages.
First Office Action dated Jan. 5, 2024, directed to CN Application No. 202080042824.9; 20 pages.
Plassat et al. U.S. Office Action dated Nov. 22, 2023, directed to U.S. Appl. No. 17/536,452; 19 pages.
First Office Action dated Dec. 8, 2023, directed to CN Application No. 202080027875.4; 21 pages.
Office Action dated Feb. 5, 2024, directed to CO Application No. NC2021/0014899; 14 pages.
Office Action dated Jan. 23, 2024, directed to EA Application No. 202192793; 4 pages.
Office Action dated Jan. 5, 2024, directed to CO Application No. NC2021/0012462; 12 pages.
Substantive Examination Report dated Mar. 5, 2024, directed to PH Application No. 1-2021-552591; 5 pages.
Office Action dated Dec. 14, 2022, directed to SA Application No. 521430528; 9 pages.
Office Action dated Dec. 15, 2022, directed to SA Application No. 521430537; 7 pages.
Office Action dated Nov. 16, 2022, directed to EA Application No. 202192793; 11 pages.
Office Action dated Nov. 16, 2022, directed to EA Application No. 202192792; 10 pages.
Amidon et al. (Mar. 1995). "A Theoretical Basis for a Biopharmaceutic Drug Classification: The Correlation of in Vitro Drug Product Dissolution and in Vivo Bioavailability," Pharmaceutical Research 12(3):413-420.
Aungst et al. (Mar. 2012). "Absorption Enhancers: Applications and Advances," The AAPS Journal 14(1): 9 pages.
International Search Report and Written Opinion mailed Jul. 22, 2020, directed to International Application No. PCT/US2020/027800; 14 pages.
International Search Report and Written Opinion mailed Jul. 22, 2020, directed to International Application No. PCT/US2020/027801; 14 pages.
Lyons et al. (Jan. 2000). "Factors limiting the oral bioavailability of N-acetylglucosaminyl-N-acetylmuramyl dipeptide (GMDP) and enhancement of absorption in rats by delivery in a water-in-oil microemulsion," International Journal of Pharmaceutics 199:17-28.
Plassat et al., Office Action dated Jul. 6, 2020, directed to U.S. Appl. No. 16/845,830; 14 pages.
Plassat et al., Office Action dated May 12, 2021, directed to U.S. Appl. No. 16/845,830; 12 pages.
Plassat et al., Office Action dated Nov. 3, 2020, directed to U.S. Appl. No. 16/845,830; 10 pages.
Tepper. (Mar. 5, 2019). "CGRP and headache: a brief review," Neurological Sciences 40(1): S99-S105.
Chaturvedula et al. (2013). "Discovery of (R)-N-(3-(7-methyl-1H-indazol-5-yl)-1-(4-(1-methylpiperidin-4-yl)-1-oxopropan-2-yl)-4-(2-oxo-1,2-dihydroquinolin-3-yl)-piperidine-1-carboxamide (BMS-742413): a potent human CGRP antagonist with superior safety profile for the treatment of migraine through intranasal delivery," Bioorganic & Medicinal Chemistry Letters 23: 3157-3161.
Office Action dated Apr. 17, 2023, directed to GB Application No. 20722945.1; 5 pages.
Office Action dated Apr. 17, 2024, directed to EP Application, No. 20723680.3; 5 pages.
Office Action dated Apr. 29, 2024, directed to CO Application No. NC2021/0012462; 12 pages.
Notice of Reasons for Rejection dated Apr. 8, 2024, directed to JP Application No. 2021-559862; 10 pages.
Office Action dated Jul. 2, 2024, directed to CO Application No. NC2021/0014899; 16 pages.
Office Action dated Jul. 6, 2024, directed to CN Application No. 202080042824.9; 15 pages.
Office Action dated May 13, 2024, directed to JP Application No. 2021-560705; 8 pages.
Office Action dated May 15, 2024, directed to IL Application No. 287084; 3 pages.
Office Action dated May 15, 2024, directed to IL Application No. 287131; 4 pages.
Second Written Opinion dated Jul. 19, 2024, directed to SG Application No. 11202110546U; 7 pages.
Examination Report No. 1 dated Feb. 20, 2025, directed to AU Application No. 2020270985; 5 pages.
Examination Report No. 1 dated Feb. 20, 2025, directed to AU Application No. 2020272059; 5 pages.
Hearing Notice dated Jan. 27, 2025, directed to IN Application No. 202127050601; 2 pages.
Office Action dated Jan. 22, 2025, directed to KR Application No. 10-2021-7036828; 17 pages.
Office Action dated Jan. 22, 2025, directed to KR Application No. 10-2021-7036823; 20 pages.
Office Action dated Nov. 11, 2024, directed to JP Application No. 2021-560705; 6 pages.
Plassat et al., U.S. Office Action dated Mar. 4, 2025, directed to U.S. Appl. No. 17/536,452; 13 pages.
Office Action dated Mar. 20, 2025, directed to PH Application No. 12021552546; 5 pages.
Office Action dated May 20, 2025, directed to SA Application No. 524452022; 6 pages.
Office Action dated May 21, 2025, directed to IL Application No. 287084; 3 pages.
Office Action dated Aug. 20, 2025, directed to EP Application No. 20722945.1; 3 pages.

(56) References Cited

OTHER PUBLICATIONS

Office Action dated Aug. 25, 2025, directed to KR Application No. 10-2021-7036823; 11 pages.
Office Action dated Aug. 25, 2025, directed to KR Application No. 10-2021-7036828; 6 pages.
Office Action dated Jul. 16, 2025, directed to CO Application No. NC2021/0012462; 20 pages.
Office Action dated Sep. 19, 2025, directed to CA Application No. 3,134,550; 5 pages.
Office Action dated Sep. 5, 2025, directed to EP Application No. 20723680.3; 4 pages.
Office Action dated Sep. 9, 2025, directed to CA Application No. 3,136,485; 5 pages.

* cited by examiner

FORMULATION FOR ORAL DELIVERY OF PROTEINS, PEPTIDES AND SMALL MOLECULES WITH POOR PERMEABILITY

CROSS-REFERENCE TO RELATED APPLICATIONS

This application is a national stage application under 35 U.S.C. § 371 of International Application No. PCT/US2020/027800, filed on Apr. 10, 2020, which claims the priority of U.S. Provisional Application No. 62/832,508, filed Apr. 11, 2019, the entire contents of each of which are incorporated herein by reference.

FIELD OF THE DISCLOSURE

This disclosure relates to a formulation for oral delivery of proteins, peptides and small molecules with poor permeability. More specifically, this disclosure relates to a pharmaceutical formulation intended for oral delivery of any molecule synthetic or natural with poor permeability or salts or solvates thereof having a therapeutic activity.

BACKGROUND OF THE INVENTION

Poorly permeable molecules are compounds that have poor absorption through the intestinal membrane. As such, they are administered intravenously or subcutaneously. Because of their poor absorption through the intestinal membrane, their clinical use is considerably restricted given the need to be administered IV and dosed several times a day (e.g., insulin for diabetics). These poorly permeable compounds are identified as BCS class III and class IV compounds in the classification proposed by Amidon G L et al in *A theoretical basis for a biopharmaceutic drug classification: the correlation of in vitro drug product dissolution and in vivo bioavailability* (Pharm Res. 1995 March; 12(3): 413-20.), which is hereby incorporated by reference in its entirety.

SUMMARY OF THE INVENTION

Applicants have developed formulations for orally administered molecules with poor permeability. The molecule may be a CGRP inhibitor. These formulations are highly beneficial for patients that require dosing several times a day. In order to prepare such formulations for oral delivery of poorly permeable CGRP inhibitors, Applicants had to overcome at least this poor permeability against the intestinal membrane; and for some of those inhibitors in particular peptides and proteins the chemical and physical instability in the gastrointestinal tract and specifically, the loss of activity due to acidic conditions in the stomach; and enzymatic degradation throughout the intestine. Accordingly, Applicants developed delayed release coated dosage form that can deliver poorly permeable CGRP inhibitors in the intestine with in-situ production of permeation enhancer to increase its bioavailability.

In U.S. Pat. No. 9,259,389, the inventors found that a digestible reverse emulsion can increase bioavailability of oligosaccharides. Unexpectedly, Applicants found that a solution of lipid excipients with a poorly permeable molecule dispersed as a powder in the formulation can allow better results of bioavailability for this specific class of molecules (i.e., BCS Class III and Class IV compounds in the classification proposed by Amidon G L et al (Pharm Res. 1995 March; 12(3):413-20.)). Specifically, Applicants found that for poorly permeable molecules, specifically BCS Class II protein and peptide compounds, the formulation without addition of water can be beneficial. Without being bound by any theory, it is believed that water tends to cause this class of the poorly permeable molecules to aggregate together. More particularly, Applicants found that when they did not include water in the formulation comprising a solution of lipid based excipients with the poorly permeable BCS Class III protein or peptide molecule or salt dispersed as a powder in the formulation, higher results of bioavailability were achieved for this specific class of molecules. In contrast, the removal of water was detrimental for saccharides of U.S. Pat. No. 9,259,389.

In addition, Applicants can increase the drug load when the API can be dispersed as a powder without the need to solubilize the active pharmaceutical ingredient ("API") in water given there is no need to solubilize the API. Furthermore, the formulation is inherently more physically stable because lipid excipients can be in solution as a sing e phase. Thus, there may be no need to add a stabilizing agent such as silicon dioxide to stabilize the phases. In some embodiments, a thickener may be added for manufacturing purposes to maintain homogeneity of the API powder in suspension during the process. In some embodiments, the thickener can be silicon dioxide. Lastly, compared to other formulations found in literature using excipients such as permeation enhancers, the formulations disclosed herein can use only generally recognized as safe excipients or already marketed ingredients.

In some embodiments, a pharmaceutical formulation comprising a synthetic or natural poorly permeable CGRP inhibitors or salt or solvate thereof in an amount 0.01-20 wt. % of the total weight of the formulation; a lipophilic phase comprising triglycerides of fatty acids in an amount of 50-80 wt. % of the total weight of the formulation; and at least one lipophilic surfactant comprising partial esters of polyol and fatty acids in an amount of 10-50 wt. % of the total weight of the formulation. In some embodiments, the synthetic or natural poorly permeable CGRP inhibitors or salt or solvate thereof is a CGRP antibody, a CGRP receptor antibody, an antigen-binding fragment from a CGRP antibody or a CGRP receptor antibody, a CGRP infusion inhibitory protein, a CGRP bio-neutralizing agent, a small molecule CGRP receptor antagonist, a small molecule CGRP inhibitor, or a polypeptide CGRP inhibitor. In some embodiments, the small molecule CGRP receptor antagonist is (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (BHV-3500). In some embodiments, the formulation comprises at least one hydrophilic surfactant with a hydrophilic lipophilic balance ("HLB") above 10 in an amount of 1-30 wt. % of the total weight of the formulation. In some embodiments, the at least one hydrophilic surfactant is selected from the group consisting of polyoxyethylene (20) monooleate, PEG 8 caprylic/capric glycerides, PEG 6 caprylic/capric glycerides, poly(ox ethylene)(4)Lauryl ether and mixtures thereof. In some embodiments, the triglycerides of fatty acids are medium chain fatty acids. In some embodiments, the lipophilic surfactant comprises a mixture of mono and diglyceride of medium chain fatty acids. In some embodiments, the formulation does not include water. In some embodiments, a delayed release pharmaceutical dosage form comprises any of the formulations described above, wherein the delayed release dosage form is a coated dosage form whose release is pH dependent. In some embodiments, a method for treating a patient comprises administering to a person in need thereof an effective amount of any of the formulations described above.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth here n prevails over the definition that is incorporated herein by reference.

BRIEF DESCRIPTION OF THE DRAWINGS

These and/or other aspects will become apparent and more readily appreciated from the following description of the embodiments, taken in conjunction with the accompanying drawings, in which.

DETAILED DESCRIPTION OF THE INVENTION

Figure 1:
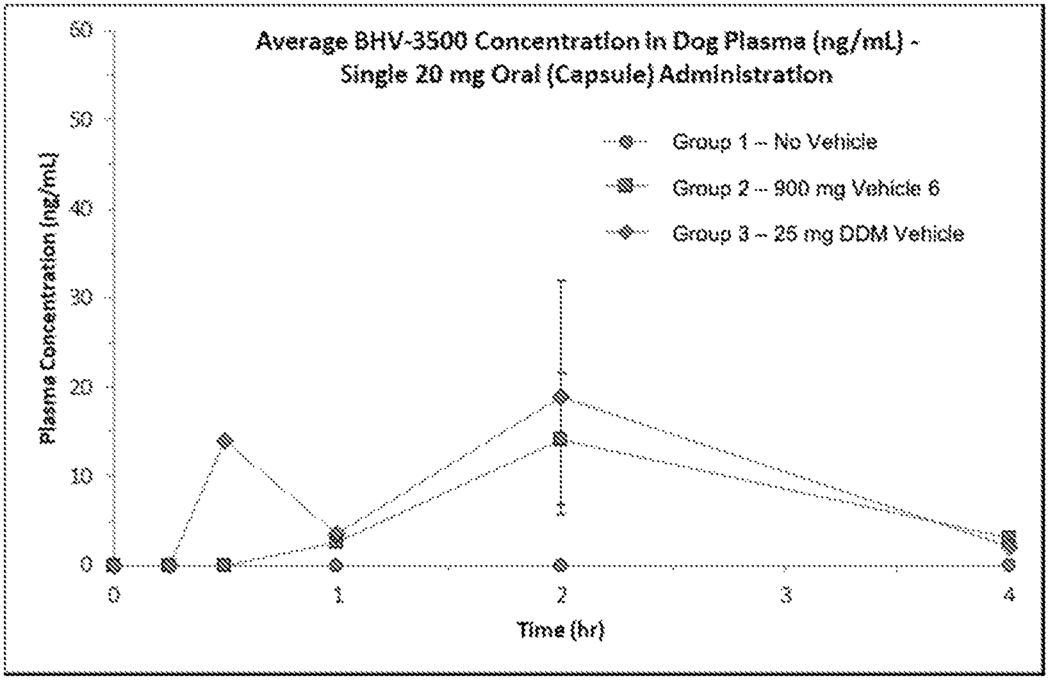
FIG. 1 is a graph showing average BHV-3500 concentration profile in dog plasma for Groups 1 to 3 (Capsule; 20 mg)

The present disclosure concerns pharmaceutical formulation intended for oral administration containing synthetic or natural poorly permeable molecules and having a therapeutic activity or a pharmaceutically acceptable additions salt or solvate thereof. These formulations can be a lipid based formulation. In addition, these formulations can be a delayed release dosage form. In some embodiments, the dosage form can be a delayed release softgel capsule, a hard-shell capsule or a combination of thereof. In some embodiments this delayed release dosage form can be an enteric released dosage form.

The formulations can include: (A) synthetic or natural poorly permeable molecules; (B) a lipophilic phase; (C) at least one lipophilic surfactant; and/or (D) at least one hydrophilic surfactant. In some embodiments, the formulations can include a chemical and/or physical stabilization agent.

Synthetic or Natural Poorly Permeable Molecules

In some embodiments, the formulation can include synthetic or natural poorly permeable molecules or any pharmaceutically acceptable salts of these poorly permeable molecules in an amount up to about 1 wt. %, about 2 wt. %, about 5 wt. %, about 10 wt. %, about 15.%, or about 20 wt. % of the total weight of the formulation. In some embodiments, the formulation can include synthetic or natural poorly permeable molecules or any pharmaceutically acceptable salts of these poorly permeable molecules in an amount of about 0.01-30 wt. %, about 0.1-30 wt. %, about 0.01-20 wt. %, about 0.1-20 wt. %, about 0.1-15 wt. %, about 0.1-10 wt. %, about 0.1-5 wt. %, about 0.1-2 wt. %, about 0.1-1 wt. %, about 0.1-0.5 wt. %, or about 0.5-1.5 wt. % of the total weight of the formulation.

The synthetic or natural poorly permeable molecule or pharmaceutically acceptable salts thereof can include: any protein, polypeptide, peptide, or small molecule with poor permeability intended for oral delivery wherein the active component according to the invention can be, but not limited to, insulin, human growth hormone, calcitonin (e.g., salmon calcitonin), an interferon such as an α-, β-, or γ-interferon, glucagon, gonadotropin-releasing hormone, enkephalins, vaccines, enzymes, hormone analogs, enzyme inhibitors, antibody and antibody mimetics. The synthetic or natural poorly permeable molecule or pharmaceutically acceptable salts thereof are those identified as BCS Class III and Class IV in the classification proposed by Amidon G L et al in A theoretical basis for a biopharmaceutic drug classification: the correlation of in vitro drug product dissolution and in vivo bioavailability (Pharm Res. 1995 March; 12(3):413-20.)

CGRP Inhibitor

The synthetic or natural poorly permeable molecule may be calcitonin gene-related peptide (CGRP) inhibitor. As used herein, the term "CGRP inhibitor" refers to a chemical entity that may be an inhibitor of a CGRP ligand or CGRP receptor. Thus, the term "CGRP inhibitor" encompasses CGRP receptor inhibitors. The CGRP inhibitor may be a CGRP inhibitor or CGRP receptor inhibitor. CGRP (calcitonin gene-related peptide) is a 37 amino acid neuropeptide, which belongs to a family of peptides that includes calcitonin, adrenomedullin and amylin. Substantial evidence has been collected to show that CGRP is implicated in pathophysiology of migraine. Clinical trials were carried out to prove that CGRP inhibitors are effective for treating migraine.

The CGRP inhibitor may be a CGRP antibody, a CGRP receptor antibody, an antigen-binding fragment from a CGRP antibody or a CGRP receptor antibody, a CGRP infusion inhibitory protein, a CGRP bio-neutralizing agent, a small molecule CGRP receptor antagonist, a small molecule CGRP inhibitor, or a polypeptide CGRP inhibitor. In an embodiment, CGRP inhibitor may be a small molecule CGRP receptor antagonist. The small molecule CGRP receptor antagonist may be (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (BHV-3500).

The CGRP inhibitor may be administered at a dose of about 1-1000 mg per day. In another aspect, the CGRP inhibitor is administered at a dose of about 1, 5, 10, 15, 20, 25, 30, 40, 50, 60, 70, 80, 90, 100, 200, 250, 300, 400, 500, 750, or 1000 mg per day. The daily dose of the CGRP inhibitor may range between any of the above val es.

Lipophilic Phase

In some embodiments, the formulation can include a lipophilic phase in an amount of up to about 50 wt. %, about 55 wt. %, about 60 wt. %, about 65 wt. %, about 70 wt. %, or about 80 wt. % of the total weight of the formulation. In some embodiments, the formulation can include a lipophilic phase in an amount of about 50-80 wt. %, about 55-75 wt. %, about 60-70 wt. %, about 62-68 wt. %, about 64-66 wt. %, or about 65 wt. % of the total weight of the formulation.

In some embodiments, the lipophilic phase can be triglycerides of fatty acids. Triglycerides of fatty acids can mean any triglycerides of saturated or unsaturated fatty acid which are pharmaceutically and orally acceptable. In some embodiments, the triglycerides of fatty acid can have the following formula:

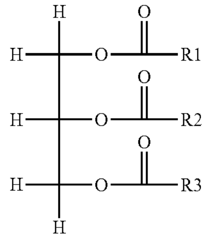

in which R1, R2, and R3 represent independently of each other the alkyl or alkenyl group of the parent fatty acid.

The fatty acid can be saturated or unsaturated. In particular, the fatty acid can be saturated since unsaturated fatty acid can give slower digestion kinetic and lower digestion percentages. Some common saturated fatty acids are indicated in the following Table 1.

TABLE 1

| Common name | IUPAC name | Chemical structure | Abbr. | Melting point (° C.) |
|---|---|---|---|---|
| Butyric | Butanoic acid | $CH_3(CH_2)_2COOH$ | C4:0 | −8 |
| Caproic | Hexanoic acid | $CH_3(CH_2)_4COOH$ | C6:0 | −3 |
| Caprylic | Octanoic acid | $CH_3(CH_2)_6COOH$ | C8:0 | 16-17 |
| Capric | Decanoic acid | $CH_3(CH_2)_8COOH$ | C10:0 | 31 |
| Lauric | Dodecanoic acid | $CH_3(CH_2)_{10}COOH$ | C12:0 | 44-46 |
| Mystiric | Tetradecanoic acid | $CH_3(CH_2)_{12}COOH$ | C14:0 | 58.8 |
| Palmitic | Hexadecanoic acid | $CH_3(CH_2)_{14}COOH$ | C16:0 | 63-64 |
| Stearic | Octadecanoic acid | $CH_3(CH_2)_{16}COOH$ | C18:0 | 69.9 |
| Arachidic | Eicosanoic acid | $CH_3(CH_2)_{18}COOH$ | C20:0 | 75.5 |
| Behenic | Docosanoic acid | $CH_3(CH_2)_{20}COOH$ | C22:0 | 74-78 |
| Lignoceric | Tetracosanoic acid | $CH_3(CH_2)_{22}COOH$ | C24:0 | |

R1, R2, and R3 can represent a straight or branched chain. In some embodiments, R1, R2, and R3 can be C3-C23 alkyl or alkenyl groups, C5-C13 alkyl or alkenyl groups, or C7-C9 alkyl or alkenyl groups. In some embodiments, fatty acids are saturated fatty acids and are medium chain fatty acids. As such, the lipophilic phase can be triglycerides of long, (such as for example soya bean oil and fish oil), medium or short (such as for example glyceryl triacetate) chain fatty acids. In some embodiments, the triglycerides can be of caprylic acid, capric acid, or mixtures thereof (such as for example the commercial product Miglyol 812®, Captex 355®, Estasan®, Neobee M5®, Labrafac CC®, and Captex 1000®). In some embodiments, the triglycerides can be triglycerides of C6-C12 fatty acids or C8-C10 fatty acids.

Lipophilic Surfactant

In some embodiments, the formulation can include at least one lipophilic surfactant in an amount of up to about 1 wt. %, about 5 wt. %, about 10 wt. %, about 15 wt. %, about 20 wt. %, about 25 wt. %, about 30 wt. %, about 35 wt. %, about 40 wt. %, about 45 wt. %, or about 50 wt. % of the total weight of the formulation. In some embodiments, the formulation can include at least one lipophilic surfactant in an amount of about 10-50 wt. %, about 15-35 wt. %, about 20-30 wt. %, about 22-28 wt. %, about 24-26 wt. %, or about 25 wt. % of the total weight of the formulation. If the formulation includes less than about 10 wt. % of the at least one lipophilic surfactant the kinetic digestion may not be optimized. If the formulation includes more than 50 wt. % of at least one lipophilic surfactant, the amount of lipophilic phase available for release of sodium caprate may not be optimal.

In some embodiments, the at least one lipophilic surfactant can be partial esters of polyol and fatty acids. Partial esters of polyol and fatty acids can mean any partial esters obtained by esterification of polyols and saturated or unsaturated fatty acids which are pharmaceutically and orally acceptable. Common saturated fatty acids are indicated in the above-mentioned Table 1. The fatty acids can be medium chain fatty acids, such as C6-C12 fatty acids, in particular caprylic and/or capric acid. The polyols can be for example propylene glycol and glycerol. For example, the partial esters of polyol and fatty acids can be propylene glycol mono- and/or di-esters of fatty acids (such as the propylene glycol monolaurate sold under the trade name Lauroglycol®, the propylene glycol monomyristate sold under the trade name Mirpyl® or the propylene glycol dicaprylate/dicaprate sold under the trade name Captex 200®, Miglyol 840®, or Neobee M-20®) and/or polyglycerol esters of fatty acids (such as the polyglyceryl oleate sold under the trade name Plurol Oleique® or Drewpol 10.10.10® or the polyglyceryl mixed fatty acids sold under the trade name Caprol ET®).

The at least one lipophilic surfactant can be partial esters of propylene glycol and fatty acids (such as for example the commercial product Capryol PGMC® and Capmul PG-8®). In some embodiments, the at least one lipophilic surfactant can be a mixture of mono and diglyceride of fatty acids, a mixture of mono and diglyceride of medium chain fatty acids, a mixture of mono and diglyceride of caprylic and/or capric acid (such as for example the commercial product Capmul MCM and Capmul MCM C8®, Imwitor 988®, Imwitor 742®), or a mixture of mono and diglyceride of capric acid (such as for example the commercial product Capmul MCM C100 or Imwitor 308®).

In some embodiments, the at least one lipophilic surfactant can be a lecithin, e.g., soybean lecithin, as but not limited to soybean lecithin.

Hydrophilic Surfactant

In some embodiments, the formulation can include at least one hydrophilic surfactant in an amount of up to about 2 wt. %, about 5 wt. %, about 8 wt. %, about 10 wt. %, about 15 wt. %, about 20 wt. %, about 25 wt. %, or about 30 wt. % of the total weight of the formulation. In some embodiments, the formulation can include at least one hydrophilic surfactant in an amount of about 0-30 wt. %, about 0-15 wt. %, about 0-10 wt. %, about 1-30 wt. %, about 5-15 wt. %, about 8-12 wt. %, about 9-11 wt. %, or about 10 wt. % of the total weight of the formulation. If the amount of the at least one hydrophilic surfactant is greater than about 30 wt. % of the formulation, the amount of lipophilic phase available for release of sodium caprate could be compromised.

In some embodiments, the at least one hydrophilic surfactant can be any hydrophilic surfactant having a hydrophilic lipophilic balance ("HLB") value above 10 which are pharmaceutically and orally acceptable. The HLB value is an empirical parameter commonly used by one skilled in the art to characterize the relative hydrophilicity and hydrophobicity of a non-ionic surfactant.

In some embodiments, the at least one hydrophilic surfactant can be phospholipids; polyoxyethylene sorbitan fatty acids derivatives, such as polyoxyethylene (20) monolaurate (sold under the trade name Tween 20®), polyoxyethylene (20) monooleate (sold under the trade name Tween 80® and/or Crillet 4®) or the polyoxyethylene (20) monopalmitate (sold under the trade name Montanox 40®); castor oil or hydrogenated castor oil ethoxylates with a HLB value above 10, such as polyoxyethylene (35) castor oil (sold under the trade name Cremophor EL®), polyoxyethylene (40) hydrogenated castor oil (sold under the trade name Cremophor RH40®), polyoxyethylene (40) castor oil (sold under the trade name Etocas 40®) or polyoxyethylene (60) hydrogenated castor oil (sold under the trade name Nikkol HCO-60®); fatty acids ethoxylates with a HLB value above 10, such as polyoxyethylene (8) stearate (sold under the trade name Myrj 45®), polyoxyethylene (30) monolaurate (sold under the trade name Tagat L®), polyoxyethylene (20) stearate (sold under the trade name Marlosol 1820®) or polyoxyethylene (15) oleate (sold under the trade name Marlosol OL15®); alcohol ethoxylates with a HLB value above 10, such as polyoxyethylene (10) oleyl ether (sold under the trade name Brij 96®), polyoxyethylene (1) oleyl ether (sold under the trade name Volpo 015®), polyoxyethylene (30) oleyl ether (sold under the trade name Marlowet OA30®) or polyoxyethylene (20) C12-C14 fatty ether (sold under the trade name Marlowet IMA20®); polyoxyethylene-polyoxypropylene co-polymers and block co-polymers with a HLB value above 10, such as the products sold under the trade name Syperonic PE L44® with a HLB value=16 or the products sold under the trade name Syperonic F127® with a HLB value=22; anionic surfactants, such as the sodium lauryl sulphate, the sodium oleate or the sodium dioctylsulphosuccinate or alkylphenol surfactants with a HLB value above 10, such as the polyoxyethylene (9-10) nonylphenol (sold under the trade name Triton N-101®) or the polyoxyethylene (9) nonylphenol (sold under the trade name Synperonic NP9®); Vitamin E; D-alpha-tocopheryl Polyethyelene glycol Succinate (TPGS); or PEG 15 Hydroxystearate (sold under the trade name Solutol HS15®).

In some embodiments, the at least one hydrophilic surfactant is a polyethoxylated surfactant. In some embodiments, the at least one hydrophilic surfactant is chosen from the group consisting of polyoxyethylene sorbitan fatty acid esters, polyoxyethylene alkyl ethers, and polyoxyethylene esters of fatty acids such as polyoxyethylene esters of glycerol and fatty acids. In some embodiments, the fatty acids are saturated or unsaturated. Common saturated fatty acids are indicated in the above-mentioned Table 1. In some embodiments, the fatty acids are medium chain fatty acids, such as C6-C12 fatty acids (e.g., lauric, caprylic, and/or capric acid).

In some embodiments, the number of ethylene oxide group units in the surfactant can be between 4 and 20. In some embodiments, the at least one hydrophilic surfactant can be chosen from the group consisting of polyoxyethylene (20) monooleate (such as for example the commercial product Tween 80®), PEG 8 caprylic/capric glycerides (such as for example the commercial product Labrasol®), PEG 6 caprylic/capric glycerides (such as for example the commercial product Softigel 767®), poly(oxyethylene(4) Lauryl ether (such as for example the commercial product Brij 30®) and mixtures thereof.

Hydrophilic Solvent

In some embodiments, the formulation can include at least one anhydrous hydrophilic solvent in an amount of up to about 15 wt. %, about 10 wt. %, about 5 wt. %, or about 1 wt. % of the total weight of the formulation to aid in solubilizing the API. In some embodiments, the formulation is free from at least one hydrophilic solvent. In some embodiments, at least one hydrophilic solvent is added, for example, to solubilize the thickener.

In some embodiments, the at least one hydrophilic solvent c be chosen from the group consisting of propylene glycol, PEG 400 diethylene glycol monoethyl ether, glycerol triacetate, ethanol, glycerol, dimethylisosorbide, N-methyl-2-pyrrolidone, poloxamers, and mixtures thereof.

Chemical and/or Physical Stabilization Agent

In some embodiments, the formulation can include at least one chemical and/or physical stabilization agent in an amount of up to about 25 wt. % of the total weight of the formulation. In some embodiments, the physical stabilization agent may be added to maintain uniformity of the API powder suspension during processing. As discussed below, the placebo formulation is physically stable given it is a single phase consisting of lipid excipients in solution, but since the API powder is dispersed as a suspension, to maintain the homogeneity, a thickener is added.

The chemical and/or physical stabilization agent can be any pharmaceutical ingredient which will improve the poorly permeable molecule chemical stability in the formulation in order to comply with the ICH Harmonized Tripartite Guideline ICH Q3B (Impurities in new drug products) requirements Current step 4 version dated Jun. 2, 2006 or which will improve the poorly permeable molecule formulation physical stability.

In some embodiments, a chemical stabilization agent can be lipophilic surfactant. For example, the chemical stabilization agent can be acetic, succinic, lactic, citric and/or tartaric esters of mono- and/or di-glycerides of fatty acids such as distilled acetylated monoglycerides (sold under the trade name Myvacet 9-45®), capryllic/capric diglyceryl succinate (sold under the trade name Miglyol 829®), mono/di-succinylated monoglycerides (sold under the trade name Myverol SMG®), glyceryl stearate citrate (sold under the trade name Imwitor 370®), glyceryl monostearate/citrate/lactate (sold under the trade name Imwitor 375®) or diacetyl tartaric asters of monoglycerides (sold under the trade name Cordatem T22®); acid ester ethoxylates formed by reacting ethylene oxide with fatty acids or glycerol esters of fatty acids with a HLB value below 10, such as polyoxyethylene (4) lauric acid (sold under the trade name Crodet 04®), polyoxyethylene (2) stearic acid (sold under the trade name Cithrol 2MS®), polyoxyethylene (3) stearic acid (sold under the trade name Marlosol 183®) or glyceryl 12 EO dioleate (sold under the trade name Marlowet G12DO®); sorbitan esters of fatty acids, such as sorbitan monolaurate (sold under the trade name Span 20® or Crill 1®) or sorbitan mono-oleate (sold under the trade name Crill 4®); transesterification products of natural or hydrogenated vegetable oil triglyceride and polyalkylene polyol with a HLB value below 10 such as polyoxyethylated apricot kernal oil (sold under the trade name Labrafil M1944CS®), polyoxyethylated corn oil (sold under the trade name Labrafil M2125CS®) or polyoxyethylated hydrogenated oil (sold under the trade name Gelucire 37/06®); or alcohol ethyoxylates with a HLB value be low 10 such as polyoxyethylated (3) oleyl ether (sold under the trade name Volpo N®), polyoxyethylated (2) oleyl ether (sold under the trade name Brij 93®) or polyoxyethylated (4) lauryl ether (sold under the trade name Marlowet LA4®).

In some embodiments, a chemical stabilization agent can be buffering agents such as citrate, phosphate, or acetate buffers and/or thickening agents such as partially hydrogenated oils, hydrogenated oils, or monoesters of unsaturated or saturated fatty acids, polyvinylpyrrolidone derivative, polyethylene oxide.

In some embodiments, a physical stabilization agent is silicon dioxide. In some embodiments, the silicon dioxide can be a colloidal silicon dioxide. Colloidal silicon dioxide is also known as fumed silicon dioxide, silica fume or pyrogenic silica. Such silicon dioxides are commercially available under the trademarks Aerosil® (Evonik industries), Cab-O-Sil® (Cabot Corporation) and Wacker HDK® (Waccker-Chemie GmbH).

In some embodiments, the formulation can include a lipidic thickener. Examples of lipid thickeners include, but are not limited to, Akosoft 36, Geleol, Gelucire, Koliwax, hydrogenated oils, or combinations thereof. In some embodiments, the formulation can include a lipidic thickener in an amount of about 5-25 wt. %, about 10-20 wt. %, about 12-18 wt. %, about 14-16 wt. %, or about 15 wt. % of the total weight of the formulation.

In some embodiments, the formulation can include povidone Examples of povidone can include different grade povidones such as K30 or K90. In some embodiments, the formulation can include povidone in an amount of about 0.5-10 wt. % about 1-10 wt. %, about 2-8 wt. %, about 4-6 wt. %, or about 5 wt. % of the total weight of the formulation.

Formulation Formation

In some embodiments, the formulation can be a liquid in the form of a solution. In some embodiments, the formulation is a solution in which the poor permeable molecule (e.g., the API) is suspended in the formulation as a powder. In some embodiments, the formulation can be a water-free reverse microemulsion or a water-free reverse emulsion. In some embodiments, the formulation is homogeneous. A homogeneous formulation can be any single or multiple phase formulation which can be used in the manufacture of a bulk fill formulation in compliance with FDA Guidance for Industry ANDAS: Blend Uniformity dated Aug. 3, 1999, and/or in the manufacture of a viable final pharmaceutical dosage form in compliance with the Content Uniformity Test criteria (excluding mass variation evaluation-European Pharmacopeia Uniformity of Dosage Units 2.9.40, USP General Chapter <905> and Japanese Pharmacopeia 6.02 Uniformity of Dosage units) and/or which can meet the compliance of stable drug substance assay results on stratified samples taken across the manufacturing process.

The formulations disclosed herein can be prepared according to the following processes. The formulation can be a blend of the different excipients. In some embodiments, excipients with the smallest quantities can be added first and the thickener can be added towards the end before the API is added. In some embodiments, the formulation is a clear solution and the API (i.e., poorly permeable molecule or salt thereof) is suspended in this formulation as a powder. The API can be a pure API crystalline, mills, micronized, lyophilized, spray dried or any method know to the person skilled in the art to obtain solid API such as atmospheric spray freeze drying. It can also be API in mixture with solid ingredients to yield a solid API such as glucoside derivative, cellulose derivative, or adsorb on another excipient like mesoporous silica, nanotubes or any materials with adsorption properties or API can be complexed such as but not limited to complexation with ion exchange resin.

The formulations disclosed herein can be digestible. As such, the glycerides can be de-esterified in 2-monoglycerides and free fatty acids by pancreatic lipase in the GI juices. The formulation can release sodium caprate that can act as permeation enhancer to promote absorption of the poorly permeable molecule loaded in the formulation. Pancreatic lipase in the presence of colipase can catalyze the lipolysis (also termed hydrolysis or de-esterification) of emulsified oils to produce fatty acids. The rate of fatty acid generation, and thus a measure of the rate of lipolysis can be followed via continuous titration with a pH-stat as described in U.S. Pat. No. 9,259,389 which is hereby incorporated in its entirety by reference. The extent of digestion after 120 min in a pancreatin solution containing a pancreatin extract having an activity of approximately 8 Tributyrin Units (TBUs) per milligram of dry powder in distilled water at the dosage of 250 mg/mt at 37.5° C.+/−0.5° C. can be such that at least about 1 mmol, about 1.5 mmol, or about 1.7 mmol of the total free fatty acid is released/g of the formulation disclosed herein.

In some embodiments, the extent of digestion after 120 min ii CPS models (and thus rate of digestion) is such that at least about 0.2 mmol, about 0.4 mmol, about 0.6 mmol, or about 0.7 mmol of the C10 free fatty acid (i.e. capric acid) is released/g of the formulation disclosed herein.

In some embodiments, the formulation disclosed herein is liquid or semi-solid (i.e. possessing a melting temperature range above room temperature) and can be orally administered to a patient in need thereof using pharmaceutical dosage form well known by the one skilled in the art. Such pharmaceutical dosage form can be gelatin or non-gelatin hardshell capsule or softgel capsule. Such capsules can include hard gelatin capsules and soft gelatin capsules and a combination of thereof (e.g., an over encapsulation of a soft gelatin capsule in a hard gelatin capsule or non-gelatin soft and/or hard capsules). This formulation can also be translated into a conventional solid dosage form by the means of techniques well known by one of ordinary skill in the art such as adsorption, hot melt granulation/coating and/or by the mean of selected carriers, diluents, additives and/or binders.

The site of absorption of the poorly permeable molecule can be in the intestine. As such, it is advantageous to co-deliver the formulation and the poor permeable molecule to its site of absorption and where the formulation is digested. In this case, dilution of the formulation in the stomach should be avoided. As a consequence, in some embodiments, the pharmaceutical dosage form is a delayed release dosage form which contains the formulation disclosed herein. Various drug delivery systems can be envisaged by one skilled in the art in order to obtain a delayed release dosage form. Various materials can enable to obtain a delayed release effect. These materials can be used to obtain matrix forms (such as described in CA2439366) or coated forms. Some delayed release and protective results can be obtained using coated dosage forms.

The various type of material which can be used to manufacture a delayed release dosage form are as follow: polymers sensitive to intestinal enzymes such as esterase and lipase (for example Salol, shellac, lipidic compounds (stearic acid, partial glycerides), camauba wax, hydrogenated castor oil) or protease (for example keratine, gluten, zein); polymers soluble in intestinal pH (this option is the most widely used in the pharmaceutical industry). These polymers can be: polysaccharides as pectin, cellulose or starch derivatives. For example, cellulose acetophtalate, hydroxypropyl methylcellulose, cellulose acetohemisuccinate, starch and amylose acetophtalate; vinylic derivatives (For example, polyvinyl acetate, polyvinyl acetophtalate); acrylic derivatives (For example, Eudragit L, Eudragit FS30D); or maleic acid copolymers.

The delayed release pharmaceutical dosage form can be pH dependent and therefore can use polymers soluble in intestinal pH. In some embodiments, the delayed release pharmaceutical dosage form can be an enteric coated dosage form, in particular an enteric coated capsule as an enteric coated soft gelatin capsule or enteric coated hard-shell capsule, more particularly an enteric coated oval soft gelatin capsule, still more particularly an enteric coated 7.5 oval or smaller soft gelatin capsule. In some embodiment, the gelatin capsule has a hardness of between 8 to 12 N according to the test indicated below, in particular of 9.5N. Smaller dosage form can be even more convenient to deliver the poorly permeable into the intestine. Delayed release dosage form with a size of 3 mm or less can go across the *pylori*'s entrance faster than larger dosage form and then release faster the poor permeable molecule in the intestine after absorption by the patient. In that case the dosage for administration may require a dosage form comprised of several small dosage forms swallowed simultaneously.

The manufacture of an enteric coated soft gelatin capsule formulation is well known by one of ordinary skill in the art such as that described in U.S. Pat. No. 9,259,389, which is hereby incorporated by reference in its entirety.

The final delayed release pharmaceutical dosage form can be monolithic or multiparticulate. That means both final dosage form (hardshell capsule, softgel capsule, or other dosage forms) and intermediate products (pellets, granules . . . ) can be coated. A particular dosage form can be a multiparticulate form (coated pellets filled into hard-shell capsules, granules or pellets used to form several small tablets) in order to minimize inter-individual variability. Examples of plasticizers for the enteric coating which can be associated with the acrylic derivatives (such as Eudragit L) are as follow: glycerol, propylene glycol, sorbitol, sorbitol/sorbitan blends, diethylphthalate, dibutylphthalate, dibutylsebacate, triethylcitrate, triacetin, acetylated monoglyceride 9-45, polyethylene glycol.

Therapeutic Activity

The formulations disclosed herein can have the same therapeutic activity as the poorly permeable molecule or salt thereof which is contained therein. Thus, this disclosure also concerns an enteric pharmaceutical dosage form disclosed herein for use as a drug.

The term "therapeutically effective amount" as used herein can refer to an amount of an agent needed to treat, ameliorate, or prevent the targeted disease condition, or to exhibit a detectable therapeutic or preventative effect. In general, the therapeutically effective dose can be estimated based on the data available for the parenteral administration of the product in humans.

Effective doses of the compounds disclosed herein may be ascertained by conventional methods. The specific dosage level required for any particular patient will depend on a number of factors; including severity of the condition being treated, the general health of the patient (i.e. age, weight and diet), the gender of the patient, the time and frequency of administration, and tolerance/response to therapy. In general, however, the daily dose (whether administered as a single dose or as divided doses) will be in the range 1 to 1000 mg per day, and most usually from 5 to 200 mg per day. Alternatively, dosages can be administered per unit body weight and in this instance a typical dose will be between 0.01 μg/kg and 50 mg/kg, especially between 10 μg/kg and 10 mg/kg, between 50 μg/kg and 2 mg/kg.

Example 1

Example compositions of the formulations disclosed herein can be found in the following Table 2:

TABLE 2

| | F1 | | F2 | | F3 | | F4 | |
|---|---|---|---|---|---|---|---|---|
| | (g) | % w/w | (g) | % w/w | (g) | % w/w | (g) | % w/w |
| API | 0.03 | 0.5 | 0.03 | 0.5 | 0.03 | 0.5 | 0.03 | 0.5 |
| Miglyol 812N | 3.18 | 63.55 | 3.24 | 64.7 | | | 2.27 | 44.8 |
| Capmul MCM | 1.09 | 21.55 | 1.24 | 24.8 | 1.54 | 29.9 | 1.25 | 24.9 |
| Tween 80 | 0.48 | 9.78 | 0.50 | 10 | | | 0.51 | 10 |
| Water | 0.25 | 4.62 | | | | | | |
| Triethylcitrate | | | | | 1.00 | 19.8 | 1.00 | 19.8 |
| Kolliphor EL | | | | | 1.76 | 34.8 | | |
| PEG 400 | | | | | 0.25 | 5 | | |
| Propylene Glycol | | | | | 0.50 | 10 | | |
| Total | 5.03 | 100 | 5.01 | 100 | 5.08 | 100 | 5.06 | 100 |

The API in the above formulations was a peptide of five amino acids with a molecular weight around 700 g/mol. In the formulations above, Miglyol, Capmul, and Triethylcitrate are permeation enhancers, Tween and Kolliphor EL are surfactants to help the kinetic of digestion and then improve the effect of Miglyol and Capmul. Water and PEG 400 and propylene glycol solubilize the API but no activity on permeability. The formulations are designed to act on the poor permeability of the molecules against the intestinal membrane. Chemical and physical instability of the gastrointestinal tract and loss of activity due to acidic conditions in the stomach can be managed by the coating.

The formulations 1-4 (F1-F4) were prepared as described in U.S. Pat. No. 9,259,389 and used a as a comparator to see the enhancement of bioavailability provided by the invention disclosed herein:

Formulation 1 preparation: The amount of API is first dissolved in water, then the Tween 80 is added. The resulting mixture is stirred to obtain a homogeneous solution. Then a solution of Miglyol 812N and Capmul MCM in defined ratio (cf. table 2) is added to the previous mixture. The final emulsion is stirred at room temperature until a homogeneous mixture (no phase separation, API fully solubilized) is obtained. This formulation should be stabilized with silicon dioxide.

Formulation 2 preparation: This formulation encompasses an inventive formulation. Capmul MCM and Miglyol 812N in the selected ratio are mixed together at room temperature. Tween 80 in the defined quantity is then added to the solution. The resulting mixture is homogenized under stirring at room temperature. The API quantity is added at the end and the final mixture is stirred until having a homogeneous suspension (no phase separation, API well dispersed into the fill).

Formulation 3 preparation: This formulation is another solution of the API with a fairly low digestibility but with an alternate permeation enhancer (triethylcitrate). The amount of API is first dissolved in a solution of PEG400 and propylene glycol, then the triethyl citrate and Kolliphor EL are added. The Capmul MCM is add d at the end. The resulting mixture is stirred at room temperature to get a homogeneous solution (no phase separation, API fully solubilized).

Formulation 4 preparation: Capmul MCM and Miglyol 812N in the selected ratio are mixed together at room temperature. Tween 80 and triethylcitrate in the defined quantity are then sequentially added to the solution. The resulting mixture is homogenized under stirring at room temperature. The API quantity is added at the end and the final mixture is stirred until a homogeneous suspension (no phase separation, API well dispersed into the fill) is obtained.

Other exemplary vehicles for API delivery may include: Crodamol GMCC-SS/Triethyl Citrate/Kolliphor EI/PEG 400/Propylene Glycol, Miglyol 12N/Crodamol GMCC-SS/Tween 80, Miglyol 812N/Crodamol GMCC-SS/Triethyl Citrate/Tween 80, Miglyol 812N/Crodamol GMCC-SS/Tween 80 with addition of water.

Digestibility of Formulations Disclosed Herein

In regard of the digestible ingredient (Miglyol 812N and Capmul MCM) ratio, more than 85%, formulations 1 (reverse emulsion) and 2 (API in suspension) are highly digestible. After 30 min of digestion, formulation 1 release 2.3 mmol of fatty acid per gram of formulation and formulation 2 release 2.1 mmol of fatty acid per gram of formulation. After 3 hours, the maximum quantity of fatty acid release by the formulation 1 and 2 is around 2.8 mmol per gram of formulation, this released quantity is the maximum release possible for all four formulations. More than 75% of fatty acid are released in less than 30 min in these two formulations. Formulation 3 (API in solution) without triglyceride (Miglyol 812N) releases the lowest quantity of fatty acid: 0.6 mmol of fatty acid per gram of formulation after 3 hours of digestion. After 30 min of digestion, only 0.3 (50%) mmol of fatty acid per gram of formulation is released. Formulation 4 releases an intermediate total quantity of fatty acid (2.0 mmol of fatty acid per gram of formulation after 3 hours of digestion) compared to the three others as the level of digestible ingredients is around 70%. 1.7 mmol of fatty acid are released after 30 min corresponding of around 85% of release within 30 min.

The following Table 3 illustrates the bioavailability of a five amino acids peptide of around 700 Da. This peptide was not sensitive to enzymatic degradation and was included into a formulation disclosed herein after administration to dogs.

TABLE 3

| Formulation | 1 | 2 | 3 | 4 |
|---|---|---|---|---|
| AUC average (n = 6) | 17694 | 59321* | 18786 | 32061 |
| Standard deviation | 7317 | 10296 | 15547 | 14439 |
| F (%) | 11 | 37 | 12 | 20 |

*n = 5

A pharmacokinetic study after intraduodenal administration of the formulations in dogs has been performed utilizing non-naive male Beagle dogs (6, 5-10 kg) to determine the bioavailability of the poorly permeable molecule, when delivered in a formulation according to the present invention. To do so, the fill formulation was administered by the mean of an endoscope under anesthesia.

The animals was anesthesied using an intra-muscular injection of Rompun at 0.03 mL/kg followed by an intramuscular injection of Zoletil 100® at 0.1 mL/kg or any similar drugs.

The test formulation was delivered intraduodenally (at least cm after the pyloric sphincter) using a plastic syringe fitted with a catheter, which is passed through a central canal of an endoscope whereas the animal was placed lying on its left side during the endoscopy. The dosage of poorly permeable molecule to administer was adjusted to each dog body weight recorded on the day of administration, such that each dog received the same dose per kg of animal body weight.

Before each administration and between each animal, the catheter was rinsed with 5 mL of NaCl 0.9% and with at least 20 mL of air. 1 mL blood samples were collected over various time points (usually pre-administration; 0.25, 0.5, 1, 2, 3, 4, 6, 8, 12 hours post-administration) from the Saphenous or cephalic veins of unanesthesised animals, into sodium citrate tubes. Blood plasma was collected after centrifugation of the samples (10 minutes, 3000 g, +4° C.) and stored at −20° C. until analysis.

Pharmacokinetic Study after Intravenous Administration:

The pharmacokinetics of the studied poor permeable molecule has been investigated after intravenous injection in order to calculate its pharmacokinetic parameters & bioavailability after oral or intraduodenal administration.

Dogs were fasted for a period of 14 hours before each intravenous administration and fed 6 hours after administration (during the kinetics measurement). For intravenous administration, the poorly permeable molecule was administered to the dogs, as a single bolus injection into a peripheral vein (Saphenous or cephalic vein) using a plastic syringe.

The dosage of poorly permeable molecule to administer was adjusted to each dog body weight recorded on the day of administration, such that each dog received the same dose per kg of animal body weight. 1 mL blood samples were collected over various time points (usually pre-administration; 0.083, 0.166, 0.25, 0.5, 1, 2, 3, 4, 6, 8, 12 h post-administration) from the Saphenous or cephalic veins of unanesthesised animals, into sodium citrate tubes. Plasma samples were prepared as detailed above (centrifugation and storage at −20° C. until further analysis).

Example 2

Example compositions of the formulations disclosed herein can b found in the following Table 4:

TABLE 4

| | F5 % w/w | F6 % w/w | F7 % w/w | F8 % w/w |
|---|---|---|---|---|
| API | | 3.0 | 6.0 | 12.0 |
| Miglyol 812N | 65 | 63.0 | 61.1 | 57.2 |
| Capmul MCM | 25 | 24.3 | 23.5 | 22 |
| Tween 80 | 10 | 9.7 | 9.4 | 8.8 |
| Total | 100 | 100 | 100 | 100 |

The API was an antibody mimetic. Formulation F5 was equivalent to placebo formulation F2. Formulations F6 to F8 were used to test increase of drug load.

Digestibility of Formulation Disclosed Herein:

In placebo formulation (F5), the release of free fatty acids is fast: more than 85% of digestible part of the formulation is digested in less than 30 minutes releasing free fatty acids (mainly C8 and C10 fatty acids) known to increase permeability through the intestinal membrane.

Formulation Manufacture:

Placebo formulation is prepared at room temperature by the addition of the three excipients together in a define ratio (cf. table 4) and mix under magnetic stirring until a single phase solution is achieved (i.e. no phase separation after 24 h without stirring).

The API selected for the Example 2 is a protein of about 12 kDa and more specifically is an antibody mimetic. The lyophilized API was grinded with a mortar and pestle prior its addition into the placebo formulation. The selected amount of API (cf. table 4) corresponding of formulation to be manufacture is added slowly to the placebo solution under continuous stirring. After the addition of the entire quantity of API, the resulting mixture is homogenized with stirring during at least 24 h.

The following Table 3 illustrates the bioavailability of the protein included into a formulation disclosed herein after administration to rats (Formulations 6,7 and 8) and dogs (Formulation 7).

TABLE 5

| | | 7 | | |
|---|---|---|---|---|
| Formulation | 6 | rat | dog | 8 |
| AUC average (n = 4) | 4954 | 9305 | 1863 | 3639 |
| Standard deviation | 6045 | 5109 | 746 | 4022 |
| F (%) | 2.2 | 2.1 | N/A | 0.4 |

The formulations 6, 7, and 8 are administered to the rat via a direct injection in the duodenum procedure. 250 mg of formulation were dosed per rat (Sprague Dawley rats, n=4). This correspond respectively to 25, 50 and 100 mg/kg body weight of antibody. Serum samples were collected at t=0, 3, 8, 24, 24, 72, 120 and 168 hours after administration. The concentration of antibody in serum samples was quantified using an antibody specific sandwich ELISA. The average AUC, Standard deviation and bioavailability (F %) are stated in the above table. These values are to be compared to a bioavailability equivalent to zero without any formulation (API in PBS buffer).

A dog study was performed with formulation 7 in four fasted non-naïve male beagle dogs. The dogs were fasted 15-16 hours prior to dose administration and food was returned approximately 1 hour post dose. Each dog received five capsules per day for six consecutive days. The dose was approximately 10 mg/kg antibody animal per day Serum samples were taken pre-dose on days 1, 2, 3, 4, 5 and 6, 2 h after dosing on days 1, 2, 3, 4, 5 and 6, and 1, 2, 4, 8, 24, 48, 96 and 168 h post dosing on day 6. The concentration of antibody in serum was quantified using an antibody specific sandwich ELISA. The results showed uptake (absorption) of antibody molecule in all four animals with some variation between individuals versus no absorption when the API was simply dissolved in PBS buffer.

Example 3

BHV-3500 (vazegepant) is a high affinity (human CGRP $K_i$=0.023 nM), selective and structurally unique small molecule CGRP receptor antagonist having the following formula I:

I

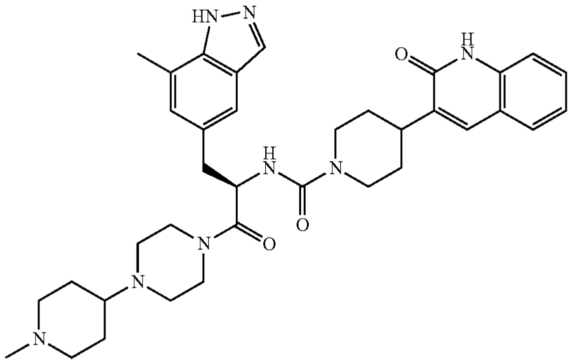

The chemical name of BHV-3500 is (R)—N-(3-(7-methyl-1H indazol-5-yl)-1-(4-(1-methylpiperidin-4-yl)piperazin-1-yl)-1-oxopropan-2-yl)-4-(2-oxo-1,2 dihydroquinolin-3-yl)piperidine-1-carboxamide. BHV-3500 is described, for example, in WO 03/104236 published Dec. 18, 2003 and U.S. Pat. No. 8,481,546 issued Jul. 9, 2013, which are incorporated herein in their entireties by reference. BHV-3500 has poor permeability and was selected as an object of the present study. BHV-3500-d8, which is an octadeuterated analog of BHV-3500 has the following formula II:

II

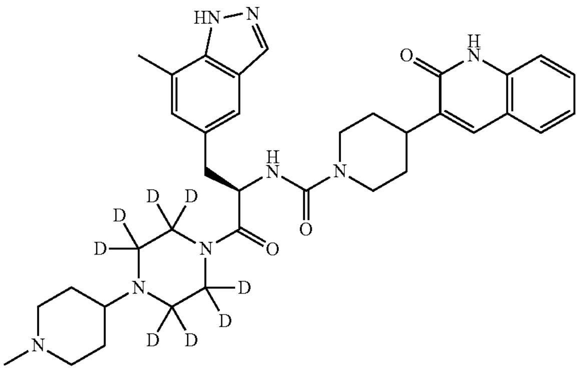

The pharmacokinetics (PK) of BHV-3500 after a single oral capsule of BHV-3500 in dogs were investigated.

Materials and Methods

1. Experimental Design and Administration

For each group, three female beagle dogs were dosed once with BHV-3500 as shown in Table 6:

TABLE 6

| Experimental Design | | | | |
|---|---|---|---|---|
| Group [a] | Test Article | Route | Formulation | Dose |
| 1 | BHV-3500 | Oral (Capsule) | None | 20 mg |
| 2 | BHV-3500 | Oral (Capsule) | 900 mg Formulation 6 [c] | 20 mg |
| 3 | BHV-3500 | Oral (Capsule) | 25 mg DDM [b] | 20 mg |

TABLE 6-continued

| Experimental Design | | | | |
|---|---|---|---|---|
| Group [a] | Test Article | Route | Formulation | Dose |
| 4 | BHV-3500 | Oral (Capsule) | None | 50 mg |
| 5 | BHV-3500 | Oral (Capsule) | 900 mg Formulation 6 | 50 mg |
| 6 | BHV-3500 | Oral (Capsule) | 25 mg DDM | 50 mg |

[a] Each group consisted of the same three beagle dogs; dosing occurred after a washout period of at least 48 hours.
[b] n-dodecyl β-D-maltoside
[c] A premade solution of SEDDS (self-emulsifying drug delivery systems) excipients (Miglyol ® 812N, Crodamol ™ GMCC-SS and Tween ® 80)

2. Blood Collection

After each dose, blood samples (approximately 3 mL from the jugular vein) for determination of plasma levels of BHV-3500 were obtained from of each dog at six time points (pre-dose; 15, 30, and 60 minutes and 2 and 4 hours post-dose. EDTA was used as the anticoagulant. Plasma samples were frozen at approximately −70'C until analyzed.

3. Reference and Internal Standards and Plasma Sample Preparation

The reference standards for BHV-3500 and BHV-3500-d8 were provided and stored at room temperature. The standards were used without further purification for the preparation of calibration standards and quality control (QC) samples for the determination of BHV-3500 concentrations in plasma samples collected during this study.

For the determination of BHV-3500 in plasma, a 50 μL aliquot from each sample was transferred into the appropriate well of a 96-well plate to which 10 μL of 50% acetonitrile (ACN) in water was added, followed by 250 μL of internal standard solution (10 ng/mL BHV-3500-d8 in ACN). After sealing the plate and vortexing for approximately 5 minutes, the plate was centrifuged at 4,000 rpm for 10 minutes at 4±4° C. A portion (100 μL) of the resulting supernatant was transferred to into the appropriate well (containing 300 μL 0.15% formic acid in water) of another 96-well plate. This plate was sealed and its contents mixed prior to instrumental analysis.

Freshly prepared BHV-3500 standard curves and QC samples were analyzed along with the study samples. Instrument calibrators were prepared by adding 10 μL of a stock BHV-3500 solution to 50 μL of blank dog plasma. Blank dog plasma was sourced from BioIVT (Hicksville, NY) and stored frozen at −20° C. Nominal calibrator concentrations ranged from 2.00 to 200 ng/mL. QC samples were prepared at concentrations of 6.00, 50.0 and 150 ng/mL. Calibrators and QC samples were processed for analysis following the extraction procedure described above.

4. Analytical Equipment and Conditions

Calibrator, QC and study samples were analyzed under LC-S/MS instrument conditions detailed in Table 7.

TABLE 7

| Instrument Operating Conditions | |
|---|---|
| SYSTEM: | Triple Quad 5500 LC-MS-MS (SCIEX; Framingham, MA) equipped with a Agilent 1100 Series LC System (Agilent Technologies, Wilmington, DE) |
| | HPLC CONDITIONS |
| HPLC Column: | Kinetex C18; 50 × 2.1 mm; 5 μm (Phenomenex, Torrance, CA) |
| Column Temperature | 25° C. |

TABLE 7-continued

| Instrument Operating Conditions | | | |
|---|---|---|---|
| Injection Volume: | 5 μL | | |
| Flow Rate: | 400 μL/min | | |
| Mobile Phase A: | 0.1% formic acid in water | | |
| Mobile Phase B: | 0.1% formic acid in acetonitrile | | |
| Program: | Time (minutes) | Mobile Phase A (%) | Mobile Phase B (%) |
| | 0.00 | 80 | 20 |
| | 0.30 | 80 | 20 |
| | 1.50 | 40 | 60 |
| | 3.50 | 40 | 60 |
| | 4.00 | 80 | 20 |
| | 7.00 | 80 | 20 |
| Run Time: | 7 minutes | | |
| Retention Time: | BHV-3500 and BHV-3500-$d_8$: approximately 0.9 minutes<br>FC-10475: approximately 2.6 minutes | | |
| | MS-MS CONDITIONS | | |
| Scan Type: | MRM | | |
| Ion Source: | Turbo Spray ESI | | |
| Polarity: | Positive | | |
| Ion Source Temperature: | 500° C. | | |
| Ion spray Voltage: | 5000 Volts | | |
| Collision Energy: | BHV-3500 and BHV-3500-$d_8$: 26 Volts | | |
| Ions monitored (Q1→Q3): | BHV-3500: 639.4→456.3<br>BHV-3500-$d_8$: 647.4→456.3 | | |
| Resolution: | Unit | | |
| Data System: | Analyst ® 1.6.3 (SCIEX; Framingham, MA) | | |

Calibration curves were calculated from the linear regression (weighting factor of 1/x2) of the analyte to internal standard peak area ratios versus the analyte concentrations. Concentrations of analyte in the samples were determined using the peak area ratios and the regression parameters of the calibration curves.

5. Pharmacokinetics

Individual animal plasma BHV-3500 concentration data at scheduled (nominal) sampling times were analyzed using the non-compartmental model f r extravascular administration with Phoenix WinNonlin software (Version 8.1; Certara, Princeton, NJ).

Elimination rate constant values (λz) were calculated by log-linear regression on data points of the terminal phase (using Phoenix WinNonlin's Best Fit Lambda Z Calculation Method option) when allowed by the data; the plasma elimination half-life (t1/2) was calculated as ln(2)/λz. Area under the plasma concentration-time curve values from time zero to the concentration at the 4 hour time point (AUC0-4 hr) were calculated by the linear-up/log-down trapezoidal rule.

Nominal dose levels were used for PK analysis. The PK parameters listed below were evaluated (as applicable and when allowed by the data).

Elimination half-life ($t_{1/2}$)

Time of occurrence of maximum plasma concentration ($T_{max}$)

Maximum plasma concentration ($C_{max}$)

Area under plasma concentration-time curve [0 to the 4 hour time point; $AUC_{0-4hr}$]

PK abbreviations and units of measure are presented in Table 8.

TABLE 8

| PK Parameter Definitions and Abbreviations | | |
|---|---|---|
| Parameter | Unit | Definition |
| Rsq | N/A | Correlation of the line fitting the terminal phase |
| $t_{1/2}$ | hr | Elimination half-life, determined by $\ln(2)/\lambda_z$ |
| $T_{max}$ | hr | Time of occurrence of maximum plasma concentration |
| $C_{max}$ | ng/mL | Maximum observed plasma drug concentration |

TABLE 8-continued

| PK Parameter Definitions and Abbreviations | | |
|---|---|---|
| Parameter | Unit | Definition |
| $AUC_{0\text{-}4\ hr}$ | hr*ng/mL | Area under the plasma concentration-time curve from time zero to the 4 hour time point |

Results

Figure 2:
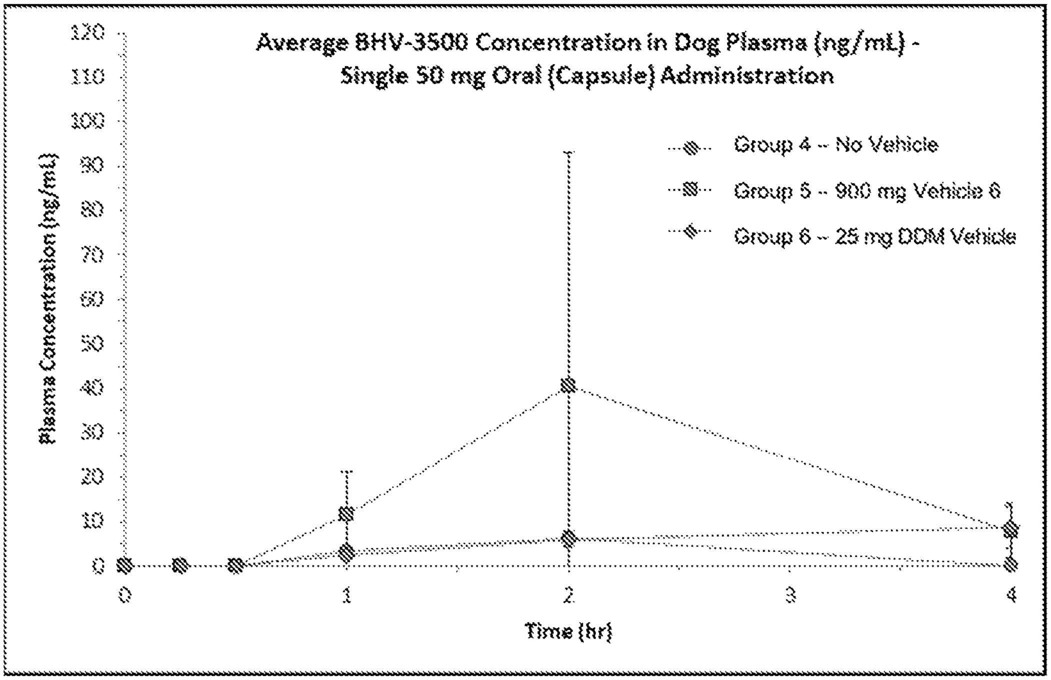
FIG. 2 is a graph showing average BHV-3500 concentration profile in dog plasma for Groups 4 to 6 (Capsule; 50 mg).

BHV-3500 concentration determinations are presented in Table 9, and are shown graphically in FIGS. 1 and 2.

TABLE 9

BHV-3500 Concentration in Dog Plasma

| | | Blood Collection Time Point | | | | | |
|---|---|---|---|---|---|---|---|
| | Female | | Hours Post-Dose | | | | |
| Group | Animal ID | Pre-Dose | 0.25 | 0.5 | 1 | 2 | 4 |
| BHV-3500 Concentration (ng/mL) | | | | | | | |
| Group 1 | 01-PWS | BQL | BQL | BQL | BQL | BQL | BQL |
| Oral (Capsule) | 05-GJU | BQL | BQL | BQL | BQL | BQL | BQL |
| 20 mg BHV-3500; | 06-VWU | BQL | BQL | BQL | BQL | BQL | BQL |
| no vehicle | Average: | BQL | BQL | BQL | BQL | BQL | BQL |
| | STD: | — | — | — | — | — | — |
| | % RSD: | — | — | — | — | — | — |
| Group 2 | 01-PWS | BQL | BQL | BQL | BQL | BQL | BQL |
| Oral (Capsule) | 05-GJU | BQL | BQL | BQL | 2.57 | 19.4 | BQL |
| 20 mg BHV-3500 in 900 | 06-VWU | BQL | BQL | BQL | BQL | 8.94 | 3.09 |
| mg of a vehicle disclosed in | Average: | BQL | BQL | BQL | 2.57 | 14.2 | 3.09 |
| Formulation 2 (SEDDS | STD: | — | — | — | — | 7.4 | — |
| Excipients) | % RSD: | — | — | — | — | 52 | — |
| Group 3 | 01-PWS | BQL | BQL | BQL | BQL | 9.60 | BQL |
| Oral (Capsule) | 05-GJU | BQL | BQL | 14.0 | 3.56 | BQL | BQL |
| 20 mg BHV-3500 in a | 06-VWU | BQL | BQL | BQL | BQL | 28.2 | 2.18 |
| vehicle of 25 mg of DDM | Average: | BQL | BQL | 14.0 | 3.56 | 18.9 | 2.18 |
| | STD: | — | — | — | — | 13 | — |
| | % RSD: | — | — | — | — | 70 | — |
| Group 4 | 01-PWS | BQL | BQL | BQL | 2.25 | 7.57 | BQL |
| Oral (Capsule) | 05-GJU | BQL | BQL | BQL | 4.25 | 4.35 | BQL |
| 50 mg BHV-3500; | 06-VWU | BQL | BQL | BQL | 3.55 | 6.61 | BQL |
| No Vehicle | Average: | BQL | BQL | BQL | 3.35 | 6.18 | BQL |
| | STD: | — | — | — | 1.0 | 1.7 | — |
| | % RSD: | — | — | — | 30 | 27 | — |
| Group 5 | 01-PWS | BQL | BQL | BQL | 6.19 | 13.8 | 6.88 |
| Oral (Capsule) | 05-GJU | BQL | BQL | BQL | 5.55 | 6.90 | 2.62 |
| 50 mg BHV-3500 in 900 | 06-VWU | BQL | BQL | BQL | 22.7 | 101 | 14.4 |
| mg of a vehicle disclosed in | Average: | BQL | BQL | BQL | 11.5 | 40.6 | 7.97 |
| Formulation 2 (SEDDS | STD: | — | — | — | 9.7 | 52 | 6.0 |
| Excipients) | % RSD: | — | — | — | 85 | 129 | 75 |
| Group 6 | 01-PWS | BQL | BQL | BQL | BQL | BQL | 5.34 |
| Oral (Capsule) | 05-GJU | BQL | BQL | BQL | 2.42 | BQL | BQL |
| 50 mg BHV-3500 in a | 06-VWU | BQL | BQL | BQL | BQL | 6.05 | 12.0 |
| vehicle of 25 mg of DDM | Average: | BQL | BQL | BQL | 2.42 | 6.05 | 8.67 |
| | STD: | — | — | — | — | — | 4.7 |
| | % RSD: | — | — | — | — | — | 54 |

BQL = below quantitation limit (2.0 ng/mL)

PK parameters are presented in Table 10.

TABLE 10

PK Parameter Analysis Results: BHV-3500

| | | PK Parameter | | | | |
|---|---|---|---|---|---|---|
| Group | Female Animal ID | Rsq | $t_{1/2}$ (hr) | $T_{max}$ (hr) | $C_{max}$ (ng/mL) | $AUC_{0\text{-}4\ hr}$ (hr*ng/mL) |
| Group 1 | 01-PWS | NC | NC | NC | NC | NC |
| Oral (Capsule) | 05-GJU | NC | NC | NC | NC | NC |

TABLE 10-continued

PK Parameter Analysis Results: BHV-3500

| Group | Female Animal ID | PK Parameter Rsq | $t_{1/2}$ (hr) | $T_{max}$ (hr) | $C_{max}$ (ng/mL) | $AUC_{0-4\ hr}$ (hr*ng/mL) |
|---|---|---|---|---|---|---|
| 20 mg BHV-3500; | 06-VWU | NC | NC | NC | NC | NC |
| no vehicle | Median/Average: | — | — | — | — | — |
| | STD: | — | — | — | — | — |
| | % RSD: | — | — | — | — | — |
| Group 2 | 01-PWS | NC | NC | NC | NC | NC |
| Oral (Capsule) | 05-GJU | NC | NC | 2 | 19.4 | NC |
| 20 mg BHV-3500 in | 06-VWU | NC | NC | 2 | 8.94 | 19.8 |
| 900 mg of a vehicle | Median/Average: | — | — | 2 | 14.2 | 19.8 |
| disclosed in Formulation | STD: | — | — | — | 7 | — |
| 2 (SEDDS Excipients) | % RSD: | — | — | — | 52 | — |
| Group 3 | 01-PWS | NC | NC | 2 | 9.60 | NC |
| Oral (Capsule) | 05-GJU | NC | NC | 0.5 | 14.0 | NC |
| 20 mg BHV-3500 in a | 06-VWU | NC | NC | 2 | 28.2 | 48.1 |
| vehicle of 25 mg of DDM | Median/Average: | — | — | 2 | 17.3 | 48.1 |
| | STD: | — | — | — | 10 | — |
| | % RSD: | — | — | — | 56 | — |
| Group 4 | 01-PWS | NC | NC | 2 | 7.57 | NC |
| Oral (Capsule) | 05-GJU | NC | NC | 2 | 4.35 | NC |
| 50 mg BHV-3500; | 06-VWU | NC | NC | 2 | 6.61 | NC |
| No Vehicle | Median/Average: | — | — | 2 | 6.18 | — |
| | STD: | — | — | — | 1.7 | — |
| | % RSD: | — | — | — | 27 | — |
| Group 5 | 01-PWS | NC | NC | 2 | 13.8 | 32.8 |
| Oral (Capsule) | 05-GJU | NC | NC | 2 | 6.90 | 17.7 |
| 50 mg BHV-3500 in | 06-VWU | NC | NC | 2 | 101 | 161 |
| 900 mg of a vehicle | Median/Average: | — | — | 2 | 40.6 | 70.6 |
| disclosed in Formulation | STD: | — | — | — | 52 | 79 |
| 2 (SEDDS Excipients) | % RSD: | — | — | — | 129 | 112 |
| Group 6 | 01-PWS | NC | NC | 4 | 5.34 | 10.6 |
| Oral (Capsule) | 05-GJU | NC | NC | 1 | 2.42 | NC |
| 50 mg BHV-3500 in a | 06-VWU | NC | NC | 4 | 12.0 | 24.0 |
| vehicle of 25 mg of DDM | Median/Average: | — | — | 4 | 6.59 | 17.3 |
| | STD: | — | — | — | 4.9 | 9 |
| | % RSD: | — | — | — | 75 | 55 |

NOTES:

[1]. $t_{1/2}$ and $T_{max}$ are reported as median; $C_{max}$ and $AUC_{0-4\ hr}$ are reported as average

[2]. NC = not calculable

SUMMARY

When BHV-3500 was administered with no vehicle to dogs at 20 mg as an oral capsule (Group 1, no vehicle) the plasma levels were below quantitation limits (BQL) at all time points. Only when the 20 mg dose was delivered in combination with Vehicle 6 and DDM (Groups 2 and 3, respectively) was BHV-3500 measurable in plasma (see FIG. 1). At this 20 mg dose, plasma BHV-3500 was BQL at the earliest 15 min time points for Group 2 and 3, with the highest concentrations seen at 2 hours post-dose with mean exposures of 14.2 and 18.9 ng/mL, respectively, which exceeds the BHV-3500 affinity for the human CGRP receptor ($K_i$=0.023 nM) by 956× (22 nM) and 1,282× (29.5 nM), respectively. When BHV-3500 was administered with no vehicle to dogs at 50 mg as an oral capsule (Group 4, no vehicle), the plasma levels were BQL at the 15 and 30 min time points, with measurable levels found at 1 and 2, but not 4 hours. When the 50 mg dose was delivered in combination with Vehicle 6 (Group 5), the plasma levels at 1 and 2 hours were increased by 3.4× to 6.6× with mean exposures of 11.5 and 40.6 ng/mL, respectively, which surpasses the BHV-3500 affinity for the human CGRP receptor ($K_i$=0.023 nM) by 782× (18 nM) and 2,763× (63.3 nM), respectively (see FIG. 2). And with Vehicle 6 the measurable plasma levels were found at 4 hours with mean exposure of 7.97 ng/mL (unlike the no vehicle condition (Group 4) where plasma levels of BHV-3500 were BQL at 4 hours). When the 50 mg dose was delivered in combination with DDM (Group 6), the plasma levels at 1 and 2 hours were similar to the no vehicle condition (Group 4). With DDM (Group 6) at 4 hours (in contrast to the no vehicle condition where at 4 hours plasma levels were BQL), measurable plasma levels of BHV-3500 were found at 4 hours with mean exposure of 8.67 ng/mL, which surpasses the BHV-3500 affinity for the human CGRP receptor ($K_i$=0.023 nM) by 590× (13.5 nM).

TABLE 11

| Group | PK Parameter $t_{1/2}$ (hr) | $T_{max}$ (hr) | $C_{max}$ (ng/mL) | $AUC_{0-4\ hr}$ (hr*ng/mL) |
|---|---|---|---|---|
| BHV-3500 | | | | |
| Group 1 Oral (Capsule) 20 mg BHV-3500; no vehicle | X | X | X | X |
| Group 2 Oral (Capsule) 20 mg BHV-3500 in 900 mg of a vehicle disclosed in Formulation 2 (SEDDS Excipients) | NC | 2 | 14.2 ± 7 | 19.8 ± 0 |
| Group 3 Oral (Capsule) 20 mg BHV-3500 in a vehicle of 25 mg of DDM | NC | 2 | 17.3 ± 10 | 48.1 ± 0 |

TABLE 11-continued

| Group | PK Parameter $t_{1/2}$ (hr) | $T_{max}$ (hr) | $C_{max}$ (ng/mL) | $AUC_{0-4\ hr}$ (hr*ng/mL) |
|---|---|---|---|---|
| Group 4 Oral (Capsule) 50 mg BHV-3500; No Vehicle | NC | 2 | 6.18 ± 1.7 | NC |
| Group 5 Oral (Capsule) 50 mg BHV-3500 in 900 mg of a vehicle disclosed in Formulation 2 (SEDDS Excipients) | NC | 2 | 40.6 ± 52 | 70.6 ± 79 |
| Group 6 Oral (Capsule) 50 mg BHV-3500 in a vehicle of 25 mg of DDM | NC | 4 | 6.59 ± 4.9 | 17.3 ± 9 |

Note:
$t_{1/2}$ and $T_{max}$ are reported as median;
$C_{max}$ and $AUC_{0-4\ hr}$ are reported as average ± standard deviation;
N = 3 (nominal);
NC = not calculated;
NA = not applicable;
X = no plasma exposure.

Description of Study Protocol

Study Title: Single dose oral capsule study of BHV-3500 in dogs.

Study Objective: To determine the pharmacokinetics of BHV-3500 capsule formulations after a single oral and sublingual dose in dogs.

Duration of Study: 3 weeks.

Test Article Formulation:

Identification. The test article is identified as BHV-3500. The test article will be supplied as capsules.

Hazard to Personnel. Routine safety procedures used for handling of hazardous or potentially hazardous chemicals will be followed to ensure the health and safety of personnel handling the test article.

Test Article Characterization. A certificate of analysis (or other appropriate documentation) verifying the identity or purity of test articles will be provided.

Dose Preparation and Analysis. No analysis will be performed on the dosing formulations.

Storage. The BHV-3500 capsules will be stored at room temperature.

Sample Disposition and Retention. All quantities of the test articles that are dispensed will be documented. Retention samples are not required for a study of this duration.

Basis for Selection of Doses of Test Articles. The test articles dose levels were selected on the basis of previous PK studies with the test articles.

Route of Administration. The test article will be administered orally (capsule), as this is one of the intended routes of administration in humans, as well as sublingually.

Disposition of Test Article. Upon completion of the study, any remaining test articles will be returned and discarded.

Experimental Design

See Table 6 above.

Test System:

Test Animals. Three (3) or 3 female beagle dogs are obtained from Ridglan Farms, Mount Horeb, WI for use in this study. All animals are immunized against distemper, type 2 adenovirus, parainfluenza, *Bordetella*, rabies, papilloma virus, and parvovirus by the supplier. Dogs will be approximately one year old and weigh approximately 8 to 12 kg at the initiation of dosing. The same 3 animals will be used for all test article administrations.

Justification. The dog is a standard species used for non-clinical toxicity studies, and is accepted by the U.S. Food and Drug Administration as a large animal (non-rodent) model system for the safety assessment of pharmacokinetics of pharmaceutical agents.

Justification for Number of Animals. The number of animals used is the minimum necessary to obtain meaningful data. To the knowledge of the Sponsor and the Study Director, conduct of this study will result in no unnecessary duplication of existing data with regard to species, test article, does(s), route, and duration of administration.

Housing. Dogs will be housed individually in pens equipped with automatic watering systems. Pens will be cleaned daily. Dogs will be housed in accordance with U.S. Department of Agriculture Welfare Standards (Title 9, Code of Federal Regulation, Part 3, 1991 Revision) and standards set forth in the Guide for the Care and Use of Laboratory Animals (National Research Council, 2011).

Food. Certified Canine Diet #2021C (Harlan Teklad, Madison, WI). Approximately 400 g of food will be made available to each dog daily for a minimum of 2 hours. Each lot of diet is analyzed for contaminants to ensure that none are present at concentrations which would be expected to interfere with the conduct or purpose of this study. Analytical data from the lots of diet to be used in the study will be retained on file at the testing facility. Dogs will be fasted prior to dosing. Food will be provided approximately one hour after dosing.

Water. Coarse-filtered City of Chicago water will be provided ad libitum to all dogs via an automatic watering system. Water is analyzed periodically for bacterial contamination and chemical composition (e.g., electrolytes, metals, etc.). Water analysis records are retained on file at the testing facility. No contaminants expected to interfere with the study are known to be present in the water.

Animal Identification. Each dog will be identified by a USDA tattoo number in the right or left ear. Each dog will also be assigned a unique number within the study. All pens will be identified by the Project Number, Animal Number, and Sex. Cage cards will be color-coded according to group.

Environmental Control. Temperature and relative humidity in the animal room will be recorded manually each day. A 12-hour light/dark cycle (maintained with an automatic timer) will be used. Animal rooms will be held within temperature and relative humidity ranges of approximately 20° C. to 25° C. and 30%-70%, respectively.

Methods:

Quarantine. Animals purchased for this study will be held in quarantine for at least two weeks prior to administration of the test article. Throughout the quarantine period, animals, will be observed at least once daily for mortality or evidence of moribundity.

Randomization. After animals have been released from quarantine, animals will be randomly assigned into groups. Prior to randomization, each dog will receive a detailed clinical observation to ensure its suitability as a test animal.

Administration. Animals in groups 1 to 2 will receive a single oral capsule administration of BHV-3500 at 20 mg/dog. Animals in groups 4 to 6 will receive a single oral (capsule) administration of BHV-3500 at a dose of 50 mg/dog. Each group will be followed by a washout period of at least 48 hours prior to the next group being dosed.

Moribundity/Mortality Observations. Prior to initiation of dosing, animals will be observed at least once daily for mortality or evidence of moribundity. Upon initiation of dosing and then throughout the remainder of the observation periods, all surviving study animals will be observed at least twice daily for mortality or evidence of moribundity and to assess their general health. Any abnormal clinical signs will be recorded. Moribundity/mortality checks will be separated by a minimum of four hours.

Moribund Animals. During the moribundity/mortality observations, any animal judged not likely to survive until the next scheduled observation period will, upon consent of the Attending Veterinarian and Study Director, be removed from the study, weighed, euthanized, and necropsied. These animals will be recorded in the study notebook as being euthanized in extremis. Dead animals will be immediately removed for necropsy and the death will be recorded in the study notebook.

Injured or Diseased Animals. Animals on test will be treated for any disease or injury in conformance with standard veterinary practice. A complete record of the circumstances and the disposition of any affected animals will be made in the study notebook. Any animal that pose a potential infectious threat to other studies will be isolated.

Clinical Observations. Clinical observation will be done approximately 1 hour after each dose administration.

Body Weight Management. Animals will be weighed prior to each dose.

Food Consumption Measurements. Individual animal food consumption will not be measured in this study.

Plasma Drug Level. Blood samples (approximately 3 mL collected from the jugular vein) for determination of plasma levels of BHV-3500 will be obtained rom each dog at six time points (pre-dose; 15, 30, and 60 minutes, 2 and 4 hours) after each dose. EDTA will be used as the anticoagulant. Plasma samples will be frozen at approximately −70° C. until analyzed at the testing center for concentration of BHV-3500. Pharmacokinetic modeling will include AUC, $t_{1/2}$, $T_{max}$, and $C_{max}$.

Postmortem. This is a non-terminal study. The dogs will returned to quarantine after the last blood collection.

Data Notebooks. All original paper data generated by the testing center will be maintained in loose-leaf notebooks. Paper data to be maintained in loose-leaf notebooks will include, but not necessarily be limited to, the following:

- the original signed Protocol and any amendments and/or deviations;
- animal receipt records;
- animal care records;
- test article data;
- blood collection data;
- TK data Data captured electronically using ToxData® (e.g., dose administration, daily moribundity/mortality and environmental data, clinical observations, body weights, etc.) will be maintained within the computer system's database; electronic copies of the ToxData®.htm files will also be backed-up onto CD-ROM(s) and the disc(s) will be maintained with the raw data.

Alteration of Design. Alterations in the Protocol may be as the study progresses in the form of a protocol amendment. No changes in the Protocol will be made without the specific written consent of the Sponsor.

Regulatory Standards and Compliance. Due to the pilot nature of this study, the study will not be conducted in compliance with Good Laboratory Practice (GLP) regulations set forth by the U.S. FDA (Title 21 of the Code of Federal Regulations, Part 38). The study will be conducted in accordance with the test center standard operating procedures.

Report. A draft version of the report will be prepared and submitted to the Sponsor for review. Information in the report will include, but not necessarily be limited to, the following:

- Copy of the approved protocol, including any amendment and/or deviations
- Species and strain of animal used
- Clinical observation data
- Body weight data
- Plasma drug level data
- Pharmacokinetic data Following Sponsor review of the draft report, a final report will be submitted to the Sponsor.

Data Retention. All raw data generated as a result of this study and a copy of the final report from the study will be archived at the testing center for a per od of one year from the date of completion of the study. The Sponsor will be responsible for all costs associated with continued storage of the archival materials in the testing center archives or for the shipment of these materials to another storage facility. The testing center QAU will maintain a complete record of the disposition of all archival materials.

Personnel. Curricula vitae for all testing center personnel involved in the execution of the study are on file at the testing center.

Protocol Approval. This protocol complies with the specific documents of the Sponsor.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined her in for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that a formulation has at most about 10 wt. %, about 15 wt. %, or about 20 wt. % of a component is meant to mean that the formulation has at most about 10 wt. %, at most about 15 wt. %, or at most about 20 wt. % of a component.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will e readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. An oral pharmaceutical formulation, comprising:
- a synthetic or natural poorly permeable calcitonin gene-related peptide (CGRP) inhibitor or salt or solvate thereof in an amount 0.01-20 wt. % of the total weight of the formulation;
- a lipophilic phase comprising triglycerides of fatty acids in an amount of 50-80 wt. % of the total weight of the formulation; and
- at least one lipophilic surfactant comprising partial esters of polyol and fatty acids in an amount of 10-50 wt. % of the total weight of the formulation,
- wherein the synthetic or natural poorly permeable CGRP inhibitor is a small molecule CGRP receptor antagonist and the small molecule CGRP receptor antagonist is (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (BHV-3500), wherein the oral pharmaceutical formulation is in a capsule.

2. The formulation of claim 1, further comprising at least one hydrophilic surfactant with a hydrophilic lipophilic balance ("HLB") above 10 in an amount of 1-30 wt. % of the total weight of the formulation.

3. The formulation of claim 2, wherein the at least one hydrophilic surfactant is selected from the group consisting of polyoxyethylene (20) monooleate, PEG 8 caprylic/capric glycerides, PEG 6 caprylic/capric glycerides, poly(oxyethylene)(4)Lauryl ether and mixtures thereof.

4. The formulation of claim 1, wherein the triglycerides of fatty acids are medium chain fatty acids.

5. The formulation of claim 1, wherein the lipophilic surfactant comprises a mixture of mono and diglyceride of medium chain fatty acids.

6. The formulation of claim 1, wherein the formulation does not include water.

7. A delayed release oral pharmaceutical dosage form comprising:
- a pharmaceutical formulation comprising:
  - a synthetic or natural poorly permeable CGRP inhibitor or salt or solvate thereof in an amount 0.01-20 wt. % of the total weight of the formulation;
  - a lipophilic phase comprising triglycerides of fatty acids in an amount of 50-80 wt. % of the total weight of the formulation; and
  - at least one lipophilic surfactant comprising partial esters of polyol and fatty acids in an amount of 10-50 wt. % of the total weight of the formulation, wherein the delayed release dosage form is a coated dosage form whose release is pH dependent,
- wherein the synthetic or natural poorly permeable CGRP inhibitor is a small molecule CGRP receptor antagonist and the small molecule CGRP receptor antagonist is (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (BHV-3500), wherein the dosage form is a capsule.

8. A method for treating a patient, comprising administering to a person in need thereof an effective amount of an oral pharmaceutical formulation in a capsule, the oral pharmaceutical formulation comprising:
- a synthetic or natural poorly permeable CGRP inhibitor or salt or solvate thereof in an amount 0.01-20 wt. % of the total weight of the formulation;
- a lipophilic phase comprising triglycerides of fatty acids in an amount of 50-80 wt. % of the total weight of the formulation; and
- at least one lipophilic surfactant comprising partial esters of polyol and fatty acids in an amount of 10-50 wt. % of the total weight of the formulation,
- wherein the synthetic or natural poorly permeable CGRP inhibitor is a small molecule CGRP receptor antagonist and the small molecule CGRP receptor antagonist is (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (BHV-3500).

9. The method of claim 8, wherein the pharmaceutical composition comprises at least one hydrophilic surfactant with a hydrophilic lipophilic balance ("HLB") above 10 in an amount of 1-30 wt. % of the total weight of the formulation.

10. The method of claim 9, wherein the at least one hydrophilic surfactant is selected from the group consisting of polyoxyethylene (20) monooleate, PEG 8 caprylic/capric glycerides, PEG 6 caprylic/capric glycerides, poly(oxyethylene)(4)Lauryl ether and mixtures thereof.

11. The method of claim 8, wherein the triglycerides of fatty acids are medium chain fatty acids.

12. The method of claim 8, wherein the lipophilic surfactant comprises a mixture of mono and diglyceride of medium chain fatty acids.

13. The method of claim 8, wherein the formulation does not include water.

14. The method of claim 8, wherein the pharmaceutical formulation is in a delayed release dosage form comprising a coated dosage form whose release is pH dependent.

* * * * *